United States Patent

Harris et al.

[11] Patent Number: 5,094,232
[45] Date of Patent: Mar. 10, 1992

[54] ANKLE BRACE WITH FLOATING PIVOT HINGE

[75] Inventors: David P. Harris, Boulder; Michael E. Berkeley, Glenwood Springs, both of Colo.

[73] Assignee: ExoFlex, Inc., St. Paul, Minn.

[21] Appl. No.: 547,595

[22] Filed: Jul. 2, 1990

Related U.S. Application Data

[63] Continuation-in-part of Ser. No. 8,196, Jan. 29, 1987, Pat. No. 4,938,206.

[51] Int. Cl.$^5$ .............................................. A61F 5/00
[52] U.S. Cl. ........................................ 602/16; 602/27
[58] Field of Search ................ 128/80 K, 80 H, 80 F, 128/80 C

[56] References Cited

U.S. PATENT DOCUMENTS

| | | | |
|---|---|---|---|
| 817,785 | 4/1906 | Kritsch | 128/80 F |
| 3,026,869 | 3/1962 | Peach | 128/80 F |
| 3,043,297 | 7/1962 | Curnin | 128/80 F |
| 4,655,201 | 4/1987 | Pirmantgen | 128/80 C |
| 4,771,768 | 9/1988 | Crispin | 128/80 H |
| 4,936,295 | 6/1990 | Crane | 128/80 H |
| 4,938,206 | 7/1990 | Harris et al. | 128/80 F |

Primary Examiner—Robert Bahr
Assistant Examiner—Lynne A. Reichard
Attorney, Agent, or Firm—Merchant, Gould, Smith, Edell, Welter & Schmidt

[57] ABSTRACT

An ankle brace for limiting flexing and pivoting movement of the ankle joint. The brace includes a soft resilient sock and a pair of brace panels positioned and retained over the sock on opposite sides of the ankle and foot. Each panel is formed by a pair of brace sections hinged together by a floating pivot axis hinge. The hinge includes pair of juxtaposed hinge plates adapted to pivot and slide with respect to each other. One of the plates is secured to the ankle section of the brace and the other is secured to the foot section of the brace. Each plate defines pivot face, with a concave groove defined in each face. The concave grooves are normally positioned at right angles with respect to each other when the pivot faces are juxtaposed. A single pivot bearing ball is positioned between the opposed pivot faces and retained in the concave grooves. A spring resiliently biases the hinge plates together against the ball pivot bearing. A second spring biases the plates for relative sliding movement. The pivot bearing ball and grooves provide a floating pivot axis for hinge rotation and sliding movement of the hinge plates, and thereby the brace sections, relative to each other.

25 Claims, 5 Drawing Sheets

ANKLE BRACE WITH FLOATING PIVOT HINGE

This application is a continuation-in-part of Ser. No. 008,196, filed Jan. 29, 1987, now issued as U.S. Pat. No. 4,938,206 to Harris et al.

BACKGROUND OF THE INVENTION

1. Field of the Invention

The present invention relates to an ankle brace and more particularly to an ankle brace structure which utilizes floating pivot hinges. More specifically, the present invention relates to a hinged ankle brace structure for supporting an ankle and foot while permitting partial or limited movement thereof.

2. Description of the Prior Art

Extensive studies have shown that the human knee and foot joints involve complex mechanisms which provide for extension and flexion movement as well as for rotary movement. These movements result from both a rotating and sliding movement as well as a pivoting movement in the knee and ankle joints. A detailed discussion of the ankle and foot joints appears in V. H. Frankel and M. Nordin "Basic Biomechanics of the Skeletal System" Chapters 6 and 7, Lea & Febiger, Philadelphia, 1980.

A floating pivot hinge is described in detail in U.S. Pat. No. 4,938,206, issued July 3, 1990, to Michael E. Berkeley, David P. Harris, and William C. McCune for "Floating Pivot Hinge and Knee Brace." The floating pivot hinge disclosed by Harris et al. is formed by a pair of juxtaposed hinge plates each having a pivot face in opposition to a pivot face on the juxtaposed plate with a concave groove in each of the faces. A pivot bearing ball is confined between the opposed faces and retained in the concave grooves. A spring, such as a Belleville spring or disk spring, biases the hinge plates together when the pivot bearing ball is positioned in the opposed grooves between the plates. The pivot bearing ball provides a floating pivot axis for hinge rotation of the hinge plates. The ball and concave grooves allows the hinge plates simultaneously to slide and pivot relative to each other. The pivot axis floats between the hinge plates, depending on the degree of pivoting and sliding movement in a wearer's knee joint as a result of flexion thereof.

OBJECTS OF THE INVENTION

It is the principal object of the present invention to provide an improved ankle brace which allows partial normal flexing and pivoting movement of the ankle and foot joint, while restraining abnormal twisting, flexing or extension of the ankle and foot.

Another object of the present invention is to provide an ankle brace of the foregoing character with a hinge construction which tracks the complex movement of the ankle with respect to the foot and leg.

It is a further object of the present invention to provide an ankle brace of the foregoing character which provides for limited movement of the wearer's foot.

Other objects and advantages of the present invention will become apparent from the following description taken in connection with the accompanying drawings.

SUMMARY OF THE INVENTION

An ankle brace incorporating a floating pivot point or pivot axis hinge is formed by a pair of opposed brace panels adapted to be secured to the wearer's leg on opposite sides of an ankle, foot and lower leg. For this purpose, the lower leg, ankle and foot heel portion are first partially covered by a sock formed of a soft resilient material such as a foam rubber material having a smooth inner surface formed by a soft knit, cloth, and a loop pile exterior surface. A zipper or seam is provided in the sock for convenience in covering the leg, ankle and foot.

A brace panel is positioned on each opposite side of the lower leg, ankle and foot encased within the sock. The brace panels are each provided with fabric hook fasteners which readily engage with the loop pile of the sock to enable the user to readily position the brace panels against the foot and ankle.

The brace panels are further tightly secured to the wearer's leg, ankle and foot by an upper leg strap which extends through slots in the brace and wraps around the calf to hold the brace tightly thereto. A second strap secures the brace panels to the leg and ankle at a point just above the ankle, while a third strap wraps around the foot to secure the brace panels tightly to the wearer's foot.

Each brace panel is articulated into two panel sections joined by a floating pivot hinge. The upper calf or ankle section is secured to the wearer's calf and ankle by the calf and ankle straps, while the lower foot section is secured to the wearer's foot by a strap which extends around the sole and arch of the foot. The straps are preferably secured to the panels so that the panels are held tightly and relatively immovably in place with respect to the leg and foot.

The pivot hinge comprises a floating pivot hinge of the type generally described in U.S. Pat. No. 4,938,206. In the ankle brace modification, the floating pivot hinge is formed by a pair of juxtaposed hinge plates one of which is secured to the upper or ankle panel section and the other is secured to the lower a foot panel section. A concave groove is recessed into each plate, one of the grooves being generally horizontal with respect to the foot and the other being generally vertical with respect to the foot so that the grooves extend generally perpendicularly to each other when the foot and ankle are in the relaxed position. The vertical groove is shorter by approximately one-half than the relatively longer horizontal groove. Both grooves are concave and provide a deeper central portion and a shallower remote portion. A single ball pivot hinge is mounted between the plates in the grooves and provides a pivot axis about which the hinge panels and brace sections coupled thereto can rotate.

One of said panels defines a peripheral housing which serves to restrict the hinge panels and the brace panel sections coupled thereto with respect to each other. A spring such as a Belleville spring biases the two plates together trapping the ball pivot hinge between them while a second biasing spring adds a force sufficient to position the hinge plates so that the ball is at the central depressed portion of each groove when the wearer's foot is relaxed. The hinge construction is defined in more detail in U.S. Pat. No. 4,938,206.

More specifically, the present invention comprises an ankle brace for a wearer's foot and ankle. The brace comprises a soft resilient sock covering the wearer's foot and ankle and a pair of brace panels secured to opposite sides of the wearer's leg and ankle. Each brace panel comprises an ankle section and a foot section. A calf strap is adapted to extend around the wearer's calf to hold said brace thereto. An ankle strap is adapted to extend around the wearer's ankle to hold said brace thereto, and a foot strap is adapted to extend around a wearer's foot to hold the brace thereto. A floating pivot axis hinge rotatably connects the respective ankle and foot brace panel sections of each pair. Each hinge comprises a pair of juxtaposed hinge plates adapted to pivot and slide with respect to each other, one of said plates being secured to the ankle brace section and the other being secured to the corresponding foot brace section. Each hinge plate has a pivot face in opposition to a pivot face on the juxtaposed plate, and a concave groove is defined in each of the faces. The concave grooves are arranged perpendicularly with respect to each other to define a generally horizontal groove and a generally vertical groove, the length of the generally horizontal groove being longer than the length of the generally vertical groove. Each groove has a deeper point and a shallower point. A single pivot bearing ball is positioned between the opposed plate faces and is retained in the concave grooves. A spring resiliently biases the hinge plates together against the pivot bearing ball when the ball is positioned in the opposed grooves between the opposing faces. The pivot bearing ball is positioned at the deeper point of each groove when the grooves are perpendicularly aligned, corresponding to the normal relaxed position of the wearer's foot.

When mounted on a wearer's leg and ankle the ankle brace precludes all but a limited scope of movement of the foot and ankle with respect to the leg. The shorter vertical groove restricts side to side movement of the wearer's foot while the longer horizontal groove restricts flexing and pointing movement of the wearer's foot. Rotational movement of the brace panels with respect to each other is restricted by limiting the pivoting movement of the hinge panels through inter-engaging stops formed on the respective hinge plates. As the wearer's foot pivots, flexes and points, the hinge tracks the swinging and sliding movement of the ankle joint. Further as the wearer walks, the hinge restricts the natural twisting movement of the ankle. Thus the brace provides for restrained and supported but limited movement of the foot and ankle.

DESCRIPTION OF THE DRAWINGS

FIG. 13 is an enlarged diagrammatic x-ray view of an ankle bone or talus and leg bone or tibia showing relative sliding and pivoting movement there between.

DESCRIPTION OF THE PREFERRED EMBODIMENT

Figure 11:
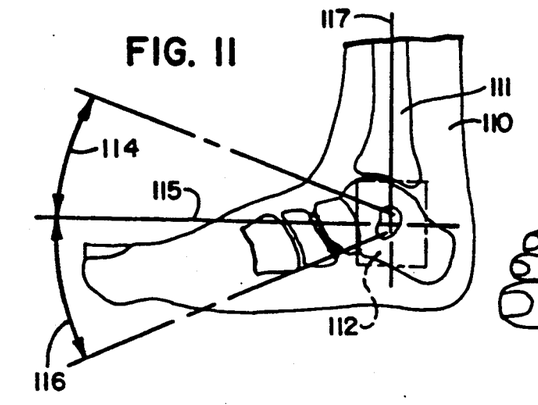
FIG. 11 is a diagrammatic representation of an elevation x-ray view of a foot showing the angle range of movement of the foot during flexing and pointing.
Figure 12:
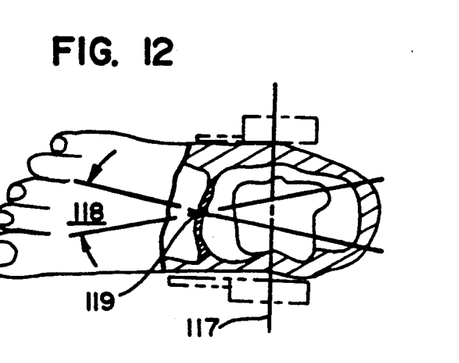
FIG. 12 is a diagrammatic x-ray representation of a foot showing the angle range of movement of the foot during twisting.
Figure 13:
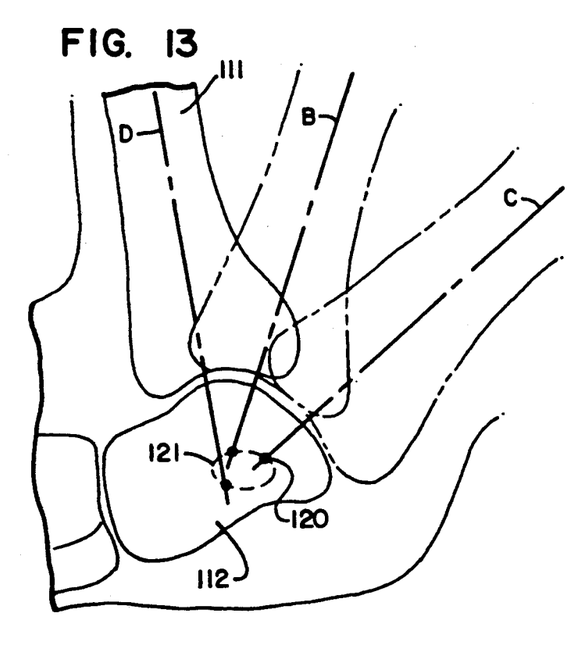

An ankle brace 50 embodying the present invention is shown in the drawings. Referring to FIGS. 1-4 the ankle brace 50 is formed by a soft yieldable foam sock 51 adapted to be inserted over the wearer's foot, ankle and lower leg, and a pair of spaced brace panels 52, 53 positioned over the sock 51 adjacent the inner and outer sides of the foot and ankle. The brace panels 52, 53 are securely held to the leg by appropriate straps which may include an upper calf strap 55, an intermediate ankle strap 56 and a lower foot strap 57. Each brace panel 52, 53 is formed in two sections, an upper ankle section 59 and a lower foot section 60, and the sections are joined by a floating pivot hinge 61. The floating pivot hinges 61 track the natural flexing and twisting movements of the ankle within predetermined limits. The brace 50 thus provides support for the ankle joint while allowing only a limited range of movement of the foot and ankle, as shown in FIGS. 11, 12 and 13.

Figures 1, 2:
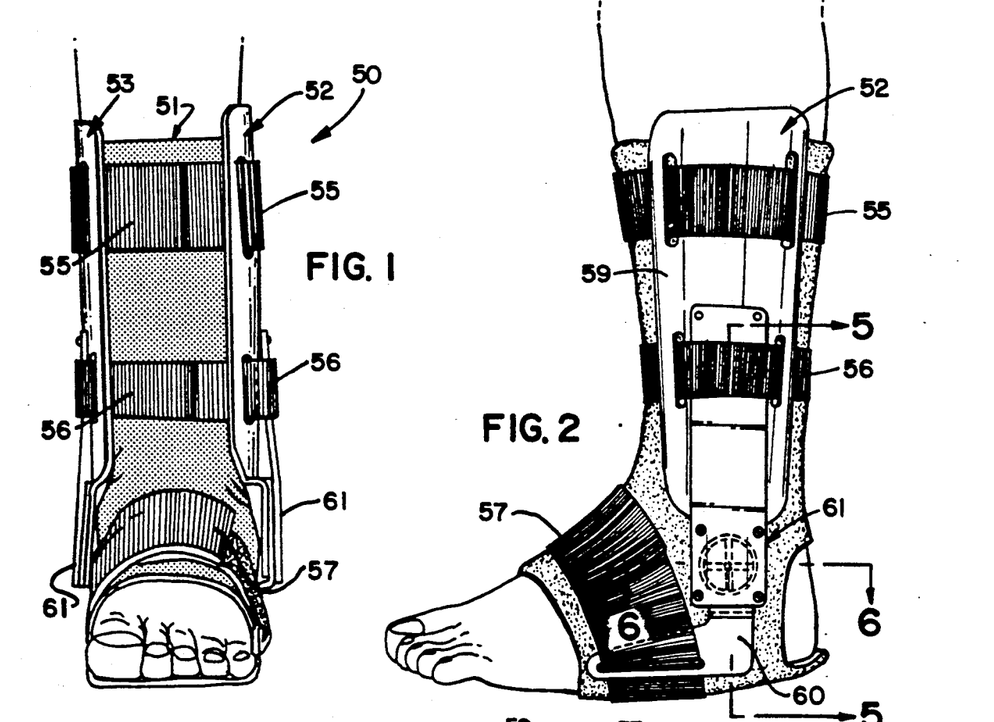
FIG. 1 is a front elevation view of an ankle brace embodying the present invention positioned on a wearer's leg.
FIG. 2 is a right side elevation view of the ankle brace shown in FIG. 1.
Figures 3, 4:
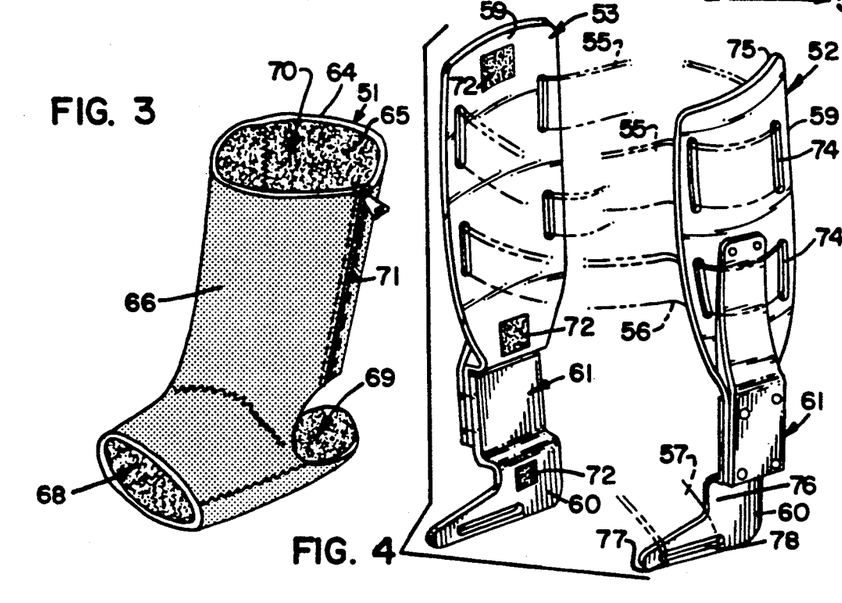
FIG. 3 is an isometric view of a sock utilized in association with the ankle brace shown in FIG. 1.
FIG. 4 is an isometric view of portions of the ankle brace shown in FIG. 1.

The soft flexible sock 51 shown in FIG. 3 comprises a foam layer 64 covered on its inner surface with a smooth soft knit fabric 65, and on its outer surface with a loop pile fabric 66. A toe opening 68, heel opening 69 and leg opening 70 are provided and a zipper 71 may be provided on the side of the sock to facilitate application of the sock to the wearer's foot. In addition to the straps 55, 56 and 57, hook pile patches 72 are secured to the inner surfaces of the brace panels at spaced points therealong for releasable engagement with the loop pile surface 66 of the sock 51. These hook pile patches secure the brace panels to the sock to prevent movement of the brace panels relative to the sock as well as to assist the securing of the brace to the wearer's foot and leg. The brace panels thus stick to the sides of the sock allowing the wearer to secure the fastening straps 55, 56 and 57.

The brace panels 52, 53 are essentially a mirror image of each other, as shown in FIG. 4. The brace may be sized for a particular foot and ankle by providing means for adjustably securing the straps to the respective brace panels.

The brace panels are, as indicated above, formed in two sections, an upper calf section 59 and a lower foot section 60 joined by the floating pivot hinge assembly 61. The upper calf section 59 is formed as a slightly curved plate or panel defining a plurality of slots 74 for receiving and retaining the straps 55, 56. The calf panel 59 defines an inner surface 75 which is curved to fit snugly against the sock 51 and the wearer's lower calf.

The foot panel 60 is generally L-shaped, defining a vertical portion 76 and a generally horizontal foot portion 77. The latter defines a strap slot 78 for receiving the foot strap 57. The foot strap 57 is desirably secured to the horizontal portion 77 to prevent slipping of the strap with respect thereto.

The straps may use any appropriate fastening mechanism, the preferred fastener being a hook and loop pile. This enables the straps not only to be secured to each other but also to grip the inner sock 51 thereby providing additional strength to the brace and enabling it to be secured tightly to the wearer's leg and foot without restricting circulation. The straps, brace panels and sock provide a unitary construction for supporting the foot and ankle.

Figure 5:
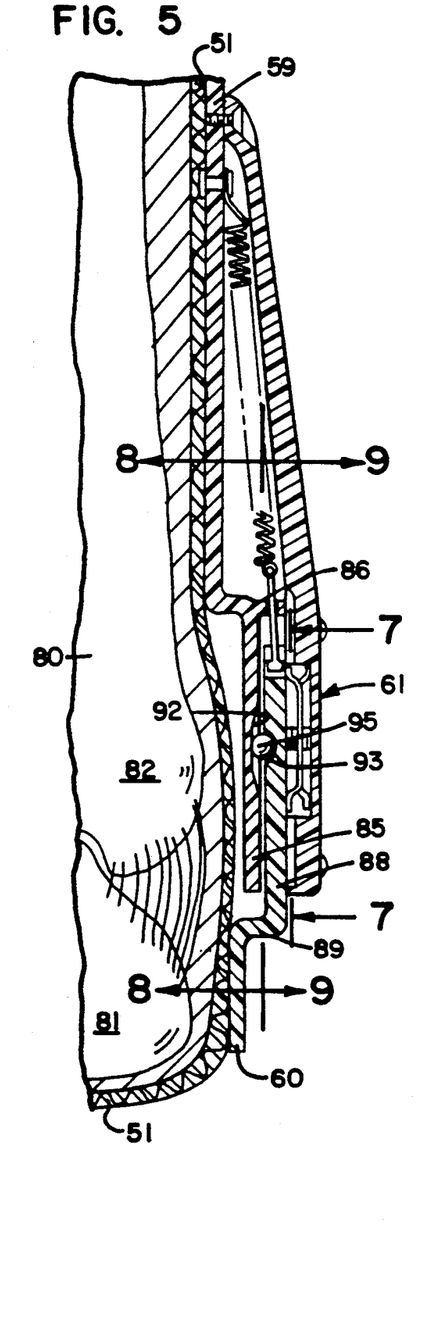
FIG. 5 is an enlarged section view taken substantially in the plane of line 5—5 on FIG. 2.
Figure 6:
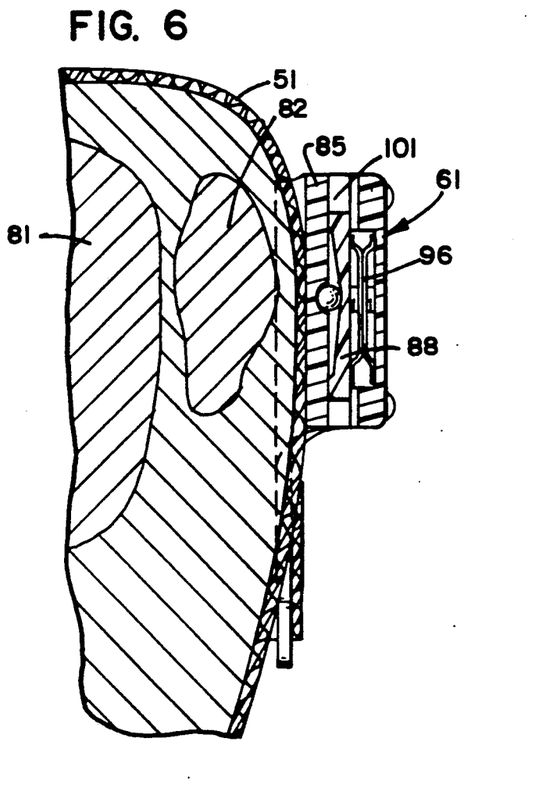
FIG. 6 is an enlarged section view taken substantially in the plane of line 6—6 on FIG. 2.
Figure 7:
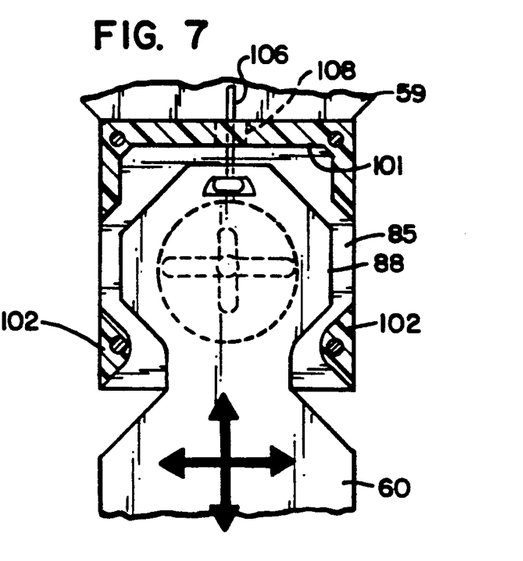
FIG. 7 is a section view taken substantially in the plane of line 7—7 on FIG. 5.
Figures 8, 9, 10:
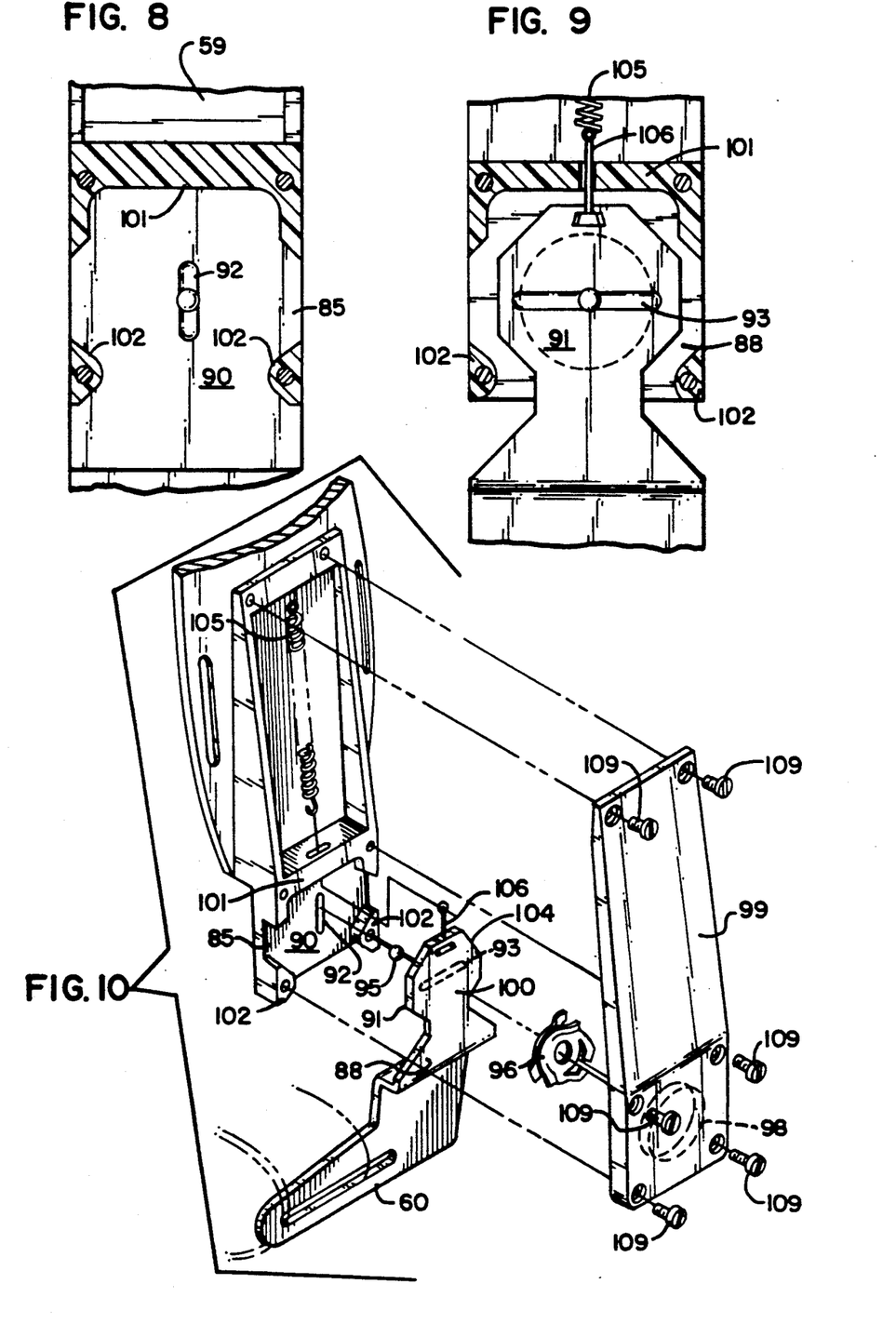
FIG. 8 is a section view taken substantially in the plane of line 8—8 on FIG. 5.
FIG. 9 is a section view taken substantially in the plane of line 9—9 on FIG. 5.
FIG. 10 is an exploded partial respective view of the ankle brace shown in FIG. 4.

The floating pivot hinge assembly 61 is shown in detail in FIGS. 5-10 inclusive. This floating pivot hinge involves the concept described and claimed in U.S. Pat. No. 4,938,206. Referring to FIG. 5 of the drawings, the hinge construction is shown in association with a tibia 80 and talus 81 forming an ankle joint. The sock 51 surrounds the ankle, and the brace calf section or panel 59 and foot section or panel 60 are positioned adjacent the tibia and talus respectively. The hinge assembly 61 is positioned adjacent the ankle joint and ankle bone 82.

The hinge assembly 61 is formed by a hinge plate 85 extending from and integral with the upper ankle panel section 59 of the brace panel 52. The hinge plate 85 is off-set from the panel section 59 by a shoulder 86 which provides for clearance between the hinge plate 85 and the ankle bone 82.

A second hinge plate 88 is integral with and extends from the lower foot section 60 of the ankle brace panel 52 and likewise is off-set therefrom by a shoulder 89. The hinge plates 85, 88 define opposed faces or surfaces 90, 91 respectively into which are cut concave recesses such as grooves 92, 93 respectively. A ball bearing pivot 95 is retained in the grooves 92, 93 and provides a floating pivot joint between the hinge plates 85, 88. As shown particularly in FIGS. 8 through 10, one concave groove 92, in a hinge plate 85, is generally vertical while the other concave groove 93, in the other hinge plate 88, is generally horizontal with respect to the tibia. When the hinge plates are placed in face-to-face relationship, the grooves are generally perpendicular to each other. It should be understood that either groove could be placed in either face.

The hinge plates 85, 88 are held in facing juxtaposed relationship with the pivot bearing ball trapped therebetween in the grooves by a biasing spring 96 retained in a recess 98 in a housing cover 99 secured to the inner hinge plate 85. The spring acts on the back surface 100 of the outer hinge plate 88 and biases the outer hinge plate 88 against the pivot ball 95. The spring 96 may be of a flat washer configuration such as a Belleville spring or similar circular leaf spring.

For constraining relative movement between the hinge plates, while allowing the hinge plates to slide and twist with respect to each other about a floating pivot point provided by the pivot ball 95, one hinge plate 85 includes a peripheral wall 101 and abutment members 102 adapted to engage the peripheral edges 104 of the other hinge plate 88. Within the limits defined by the wall 101 and abutments 102, the hinge plates can twist and slide relative to each other in a full floating relationship about the floating pivot point defined by the pivot ball 95.

Because of the nature of the foot and ankle joint, it is desirable to bias the foot panel section 60 upwardly, and for this purpose a biasing spring 105 is secured between the hinge plate 88 secured to the foot section 60 and the ankle section 59. The housing cover 99 encloses the biasing spring 105 to prevent it from becoming tangled in the straps or external matter. A hinge post 106 extends upwardly from the hinge plate 88 through an aperture 108 in the retaining wall 101 where it is connected to the biasing spring 105. The cover 99 is secured to the upper brace section by appropriate fasteners 109.

The constraining walls 101, 102 on inner hinge plate 85 co-act with the generally octagonal peripheral edge of the outer hinge plate 88 to provide for limited twisting and sliding movement between the two hinge plates. The twisting and sliding movement between the plates is further restricted by the relationship of the concave grooves and single pivot ball bearing 95. The pivoting, sliding, twisting motion controlled by the ankle brace is schematically depicted in FIGS. 11-14 which illustrate a foot 110, tibia 111 and astragalus or talus 112. As shown in FIG. 11, the foot 110 can flex through a vertical angle 114 above the horizontal 115 and point through a vertical angle 116 relative to the horizontal 115. The vertical axis 117 extends through the foot although the swinging movement of the foot from side to side through a horizontal angle 118 is about a reference point 119 spaced from the vertical axis 117 through the tibia as shown in FIG. 12.

Figure 13A:
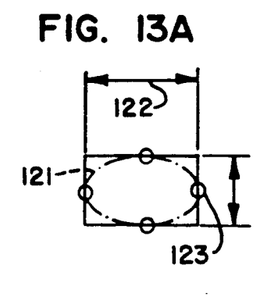
FIG. 13A is a diagrammatic representation of the center pivot points of movement shown in FIG. 13.
Figure 14:
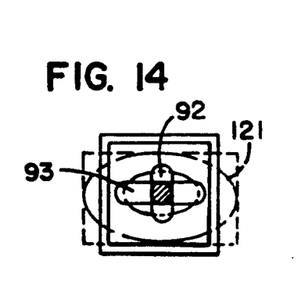
FIG. 14 is a diagrammatic representation of the hinge plates of the ankle brace shown in FIG. 1 relative to the locus of pivoting movement shown in FIG. 13A.
Figure 14A:
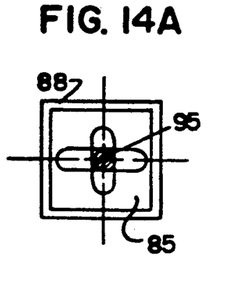
FIGS. 14A, 14B, 14C and 14D are diagrammatic representations of the relative movement of the hinge plates of the ankle brace shown in FIG. 1.
Figure 14B:
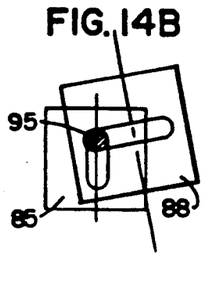
Figure 14C:
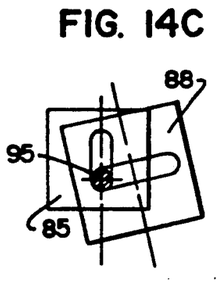
Figure 14D:
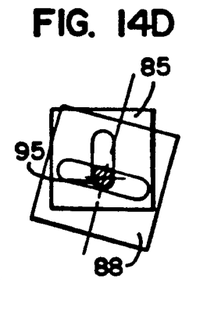

The sliding movement of the tibia 111 with respect to the talus 112 is illustrated in FIG. 13. As the tibia swings and pivots relative to the talus, the pivot point 120 defines a generally J-shaped path 121 which may be extrapolated to an oval as shown in FIG. 13A. This path 121 is longer, 122, than it is deep, 123. The comparison of the path 121 to the hinge plates and concave slots 92, 93 is depicted in FIG. 14. FIGS. 14A-14D depict the movement of the floating pivot point defined by the ball bearing 95 as it tracks the pivoting movement of the ankle joint. Referring to FIG. 13, the foot and tibia extend from one extreme C when the foot is at full point through an intermediate position B when the foot is partially pointed to a further extreme position D when the foot is flexed. This position of the foot corresponds to the hinge positions as shown in FIGS. 14B, 14C and 14D respectively. FIG. 14A illustrates the foot in a normal or relaxed position as shown in FIG. 11.

Figure 15:
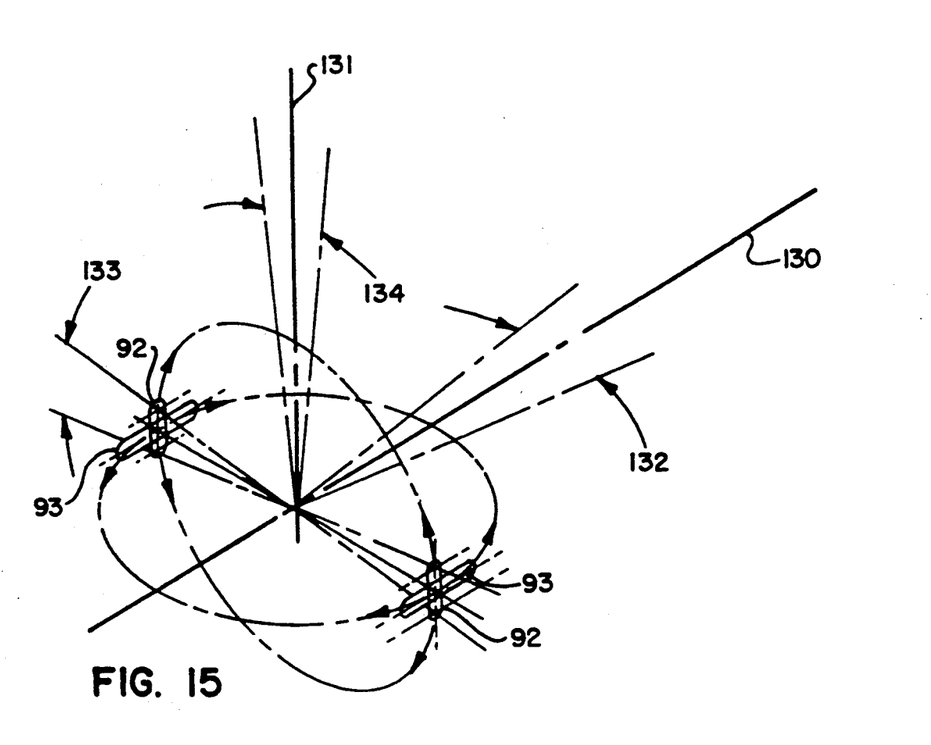
FIG. 15 is a diagrammatic representation of the locus of points of movement of a foot, ankle and leg joint in relationship to the hinge plates shown in FIG. 1.
Figure 16:
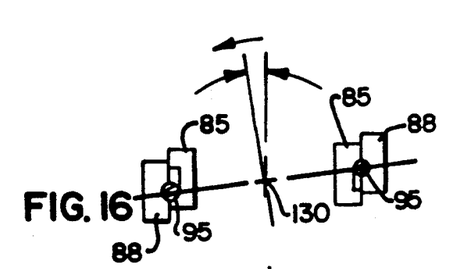
FIGS. 16, 17, 18, 19, 20 and 21 are diagrammatic representations of the relative movement of the hinge plates during flexing and twisting of an ankle joint.
Figure 17:
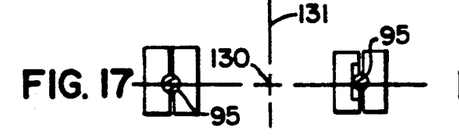
Figure 18:
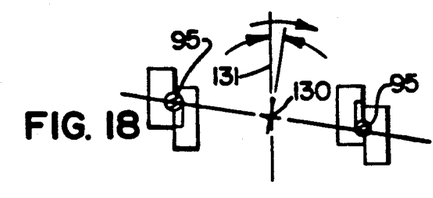
Figures 19, 20:
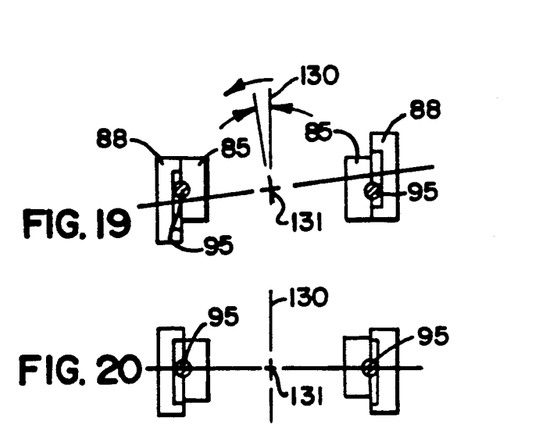
Figure 21:
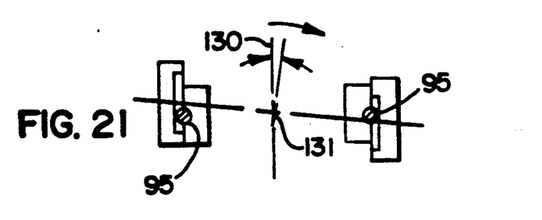

The movement of the foot is further schematically illustrated in FIG. 15 which illustrates schematically both pointing and flexing as well as twisting about a vertical and a horizontal axis. FIGS. 16-21 illustrate the twisting movement of the foot about a horizontal axis resulting from effective side to side movement of the foot. In FIG. 15 there is illustrated a horizontal axis of movement 130 and a vertical axis 131. The foot can twist about either of these axes within the limits provided by the pivot hinge when the ankle brace is secured to the foot. The twisting of the foot and ankle about a vertical axis parallel to the tibia is illustrated by the included angle 132. Side to side twisting of the foot about a horizontal axis 130 is illustrated by the included angle 133. Pointing and flexing of the foot about a horizontal axis perpendicular to the longitudinal axis is illustrated by the included angle 134. The various positions of the hinge plates are schematically demonstrated in FIGS. 16-21. FIGS. 16, 17 and 18 demonstrate a side to side twisting action about the longitudinal axis of the foot. FIGS. 19-21 illustrate the pivoting of the foot in a horizontal plane about the vertical axis parallel to the tibia.

The invention further contemplates the possible use of a concave recess or depression in one of the hinge plate faces or surfaces with the pivot ball retained in a depression or hole in the surface of the other hinge plate. The concave depression or recess may be circular, defining a conical inclined plane surface, or generally oval or rectangular in configuration with surfaces sloping from a deepest central portion outwardly at varying degrees of slope to the peripheral edges of the depression. The configuration must be such that the hinge tracks the natural complex pivoting, sliding and twisting movement of the joint being supported.

While a certain illustrative embodiment of the present invention has been shown in the drawings and described in detail in the specification, it should be understood that there is no intention to limit the invention to the specific form and embodiments disclosed. On the contrary, the intention is to cover all modifications, alternative constructions, equivalents and uses falling within the spirit and scope of the invention as expressed in the appended claims.

We claim:

1. An ankle brace for supporting a wearer's foot and ankle while affording limited movement thereof, said brace comprising a pair of brace panels adapted to be secured to opposite sides of a wearer's leg and ankle, each said brace panel comprising an ankle section and a foot section, a calf strap secured to said ankle section and adapted to extend around the wearer's calf to hold said brace thereto, an ankle strap secured to said ankle section and adapted to extend around the wearer's ankle to hold said brace thereto, a foot strap secured to said foot section and adapted to extend around a wearer's foot to hold the brace thereto, a floating pivot axis hinge rotatably connecting the respective ankle and foot sections of each brace panel, each said hinge comprising a pair of juxtaposed hinge plates adapted to pivot and slide with respect to each other, one of said plates being secured to said ankle section and the other being secured to the corresponding foot section, each said plate having a pivot face in opposition to a pivot face on the juxtaposed plate, a concave groove in each of said faces, said concave grooves being arranged perpendicularly with respect to each other to define a generally horizontal groove and a generally vertical groove, the length of the generally horizontal groove being longer than the length of the generally vertical groove, a single pivot bearing ball positioned between said opposed faces and retained in said concave grooves, and means resiliently biasing said hinge plates together against said pivot bearing ball when said ball is positioned in said opposed grooves between said opposing faces, said pivot bearing ball being located at the deeper point of each said concave groove when said grooves are perpendicularly aligned corresponding to the normal relaxed position of the wearer's foot, whereby said pivot bearing ball provides a floating pivot axis for hinge rotation of said hinge plates and thereby said brace arms relative to each other, said concave grooves allowing said hinge plates to slide relative to each other and simultaneously pivot relative to each other about said floating pivot axis provided by said ball during limited flexion, extension and twisting of the wearer's foot.

2. An ankle brace as defined in claim 1 wherein said biasing means comprises a spring.

3. An ankle brace as defined in claim 1 further including means for limiting pivotal and sliding movement of said ankle and foot brace sections relative to each other about said floating pivot axis.

4. An ankle brace as defined in claim 3 wherein said limiting means comprises a peripheral wall defined on one of said brace section hinge plates for engaging a peripheral edge of the other brace section thereby and limiting swinging and sliding movement thereof relative to said one brace section.

5. An ankle brace as defined in claim 1 further comprising a soft, flexible sock covering the wearer's foot, ankle and lower leg with the brace panels and straps being secured to the external surface thereof.

6. An ankle brace as defined in claim 5 including means for fastening said brace panels to said sock.

7. An ankle brace as defined in claim 6 wherein said fastening means comprises hook and loop pile fasteners.

8. An ankle brace as defined in claim 1 further comprising means for biasing said foot section hinge plate for relative upward vertical sliding movement with respect to said ankle section hinge plate.

9. An ankle brace for supporting a wearer's foot and ankle while providing for limited movement thereof, said brace comprising a soft, flexible sock covering the foot and ankle, a pair of brace panels adapted to be secured over said sock to opposite sides of a wearer's leg, ankle and foot, each brace panel comprising an ankle section and a foot section, a calf strap adapted to extend around the wearer's calf to hold said brace thereto, an ankle strap adapted to extend around the wearer's ankle to hold said brace thereto, a foot strap adapted to extend around a wearer's foot to hold the brace thereto, and floating pivot axis hinges rotatably connecting the respective ankle and foot brace panel sections of each pair, each said hinge comprising a pair of juxtaposed hinge plates adapted to pivot and slide with respect to each other, one of said plates being secured to said ankle section and the other being secured to the corresponding foot section, each said plate having a pivot face in opposition to a pivot face on the juxtaposed plate, a concave groove in each of said faces, said concave grooves being arranged perpendicularly with respect to each other to define a generally horizontal groove and a generally vertical groove, the length of the generally horizontal groove being longer than the length of the generally vertical groove, each said groove having a deeper point and a shallower point, a single pivot bearing ball positioned between said opposed faces and retained in said concave grooves, means resiliently biasing said hinge plates together against said pivot bearing ball when said ball is positioned in said opposed grooves between said opposing faces, said pivot bearing ball being located at the deeper point of each said groove when said grooves are perpendicularly aligned corresponding to the normal relaxed position of the wearer's foot, means biasing said foot section plate upwardly with respect to said ankle section plate, and means on said ankle section plate for engaging said foot section plate for limiting relative movement therebetween, whereby said pivot bearing ball provides a floating pivot axis for hinge rotation of said hinge plates and thereby said brace arms relative to each other, said concave grooves allowing said hinge plates to slide relative to each other and simultaneously pivot relative to each other about said floating pivot axis provided by said ball during limited flexion, extension and twisting of the wearer's foot.

10. An ankle brace for supporting a wearer's foot and ankle, while providing for limited normal movement thereof, said brace comprising a soft flexible sock covering the wearer's ankle, lower leg and foot, a pair of brace panels adapted to be secured to opposite sides of the leg, ankle and foot, each brace panel comprising an ankle section and a foot section, a calf strap adapted to extend around the wearer's calf to hold said brace thereto, an ankle strap adapted to extend around the wearer's ankle to hold said brace thereto, a foot strap adapted to extend around a wearer's foot to hold the brace thereto, floating pivot axis hinges rotatably connecting the respective ankle and foot sections of each brace panel, each said hinge comprising a pair of juxtaposed hinge plates adapted to pivot and slide with respect to each other, one of said plates being secured to said ankle section and the other being secured to the corresponding foot section, each said plate having a pivot face in opposition to a pivot face on the juxtaposed plate, a concave groove in each of said faces, said concave grooves being arranged perpendicularly with respect to each other and defining a generally horizontal groove in one plate and a generally vertical groove in the other plate, the length of the generally horizontal groove being longer than the length of the generally vertical groove, a single pivot bearing ball positioned between said opposed faces and retained in said concave grooves, means resiliently biasing said hinge plates together against said pivot bearing ball when said ball is positioned in said opposed grooves between said opposing faces, said pivot bearing ball being located at the deeper point of each said groove when said grooves are perpendicularly aligned corresponding to the normal relaxed position of the wearer's foot, means resiliently biasing said foot section plate upwardly with respect to said ankle section plate, and means operatively restricting pivoting and sliding movement of said plates relative to each other whereby said pivot bearing ball and concave grooves provide a floating pivot axis for hinge rotation of said hinge plates and thereby said brace panel sections relative to each other, said concave grooves allowing said hinge plates to slide relative to each other and simultaneously pivot relative to each other about said floating pivot axis provided by said ball to limit flexion, extension and twisting of a wearer's foot supported by the brace.

11. An ankle brace as defined in claim 10 wherein each said biasing means comprises a spring.

12. An ankle brace as defined in claim 10 wherein said restricting means comprises a housing defined on one of said brace sections hinge plate and having means defining retaining walls around the periphery of said brace section for engaging the peripheral wall of the other brace section and limiting swinging and pivoting movement thereof relative to said one brace section.

13. An ankle brace as defined in claim 10 wherein said brace panels include releasable fasteners adapted to engage said sock for retaining said panels thereon.

14. An ankle brace adapted to limit flexing and pivoting movement of the ankle joint and foot comprising a soft flexible sock covering the ankle joint and foot, a pair of brace panels adapted to be positioned and retained on opposite sides of a wearer's sock covered ankle and foot, each panel comprising a pair of brace sections hinged together by a floating pivot axis hinge, said hinge comprising a pair of juxtaposed hinge plates adapted to pivot and slide with respect to each other, one of said plates being secured to one brace section and the other being secured to the other brace section, each said plate having a pivot face in opposition to a pivot face on the juxtaposed plate, a concave groove in each of said faces, said concave grooves being normally positioned at right angles with respect to each other, said grooves being of unequal length with the generally horizontal groove being longer than the generally vertical groove, a single pivot bearing ball positioned between said opposed faces and retained in said concave grooves, means for resiliently biasing said hinge plates together against said ball pivot bearing when said ball is positioned in opposed grooves between said opposing faces, and means for limiting pivoting and sliding movement relative to each other whereby said brace provides as floating pivot axis and limited rotation and sliding movement relative to each other for restraining and limiting the movement of an ankle and foot supported thereby.

15. An ankle brace as defined in claim 14 wherein said limiting means comprises a peripheral wall defined on one of said brace sections, and means defined on the other of said brace sections for engaging said wall for limiting swinging movement of the brace sections with respect to said each other.

16. An ankle brace adapted to limit flexing and pivoting movement of the ankle joint and foot comprising a soft flexible sock covering the ankle joint and foot, a pair of brace panels adapted to be positioned and retained on opposite sides of a wearer's sock covered ankle and foot, each panel comprising a pair of brace sections hinged together by a floating pivot axis hinge for restraining and limiting the movement of an ankle and foot supported thereby.

17. An ankle brace as defined in claim 16 wherein said hinge includes means for limiting pivotal and sliding movement of said brace sections relative to each other about said floating pivot axis.

18. An ankle brace as defined in claim 17 wherein said limiting means comprises walls defined on one of said brace sections hinge plate for engaging peripheral edges of the other brace section and limiting swinging and sliding movement thereof relative to said one brace section.

19. An ankle brace for supporting a wearer's foot and ankle while affording limited movement thereof, said brace comprising a pair of brace panels adapted to be secured to opposite sides of a wearer's leg and ankle, each said brace panel comprising an ankle section and a foot section, a calf strap secured to said ankle section and adapted to extend around the wearer's calf to hold said brace thereto, an ankle strap secured to said ankle section and adapted to extend around the wearer's ankle to hold said brace thereto, a foot strap secured to said foot section and adapted to extend around a wearer's foot to hold the brace thereto, and a floating pivot axis hinge rotatably connecting the respective ankle and foot sections of each brace panel said hinge and allowing said brace sections to slide relative to each other and simultaneously pivot relative to each other to provide for limited controlled flexion, extension and twisting of the wearer's foot.

20. An ankle brace as defined in claim 19 further comprising a soft, flexible sock covering the wearer's foot, ankle and lower leg with the brace panels and straps being secured to the external surface thereof.

21. An ankle brace as defined in claim 20 including means for fastening said brace panels to said sock.

22. An ankle brace as defined in claim 21 wherein said fastening means comprises hook and loop pile fasteners.

23. An ankle brace as defined in claim 19 further comprising means for biasing said foot section for relative upward vertical sliding movement with respect to said ankle section.

24. An ankle brace for supporting a wearer's foot and ankle while providing for limited movement thereof, said brace comprising a soft, flexible sock covering the foot and ankle, a pair of brace panels adapted to be secured over said sock to opposite sides of a wearer's leg, ankle and foot, each brace panel comprising an ankle section and a foot section, means for securing said brace to the wearer's calf, ankle and foot, and floating pivot axis hinges rotatably connecting the respective ankle and foot brace panel sections of each pair, for limiting pivotal and sliding movement of said brace sections relative to each other about a floating pivot axis thereby to control and limit flexion, extension and twisting of the wearer's foot.

25. An ankle brace for supporting a wearer's foot and ankle while providing for limited movement thereof, said brace comprising a soft, flexible sock covering the foot and ankle, a pair of brace panels adapted to be secured over said sock to opposite sides of a wearer's leg, ankle and foot, each brace panel comprising an ankle section and a foot section, means for securing said brace to the wearer's calf, ankle and foot, and floating pivot axis hinges rotatably connecting the respective ankle and foot brace panel sections of each pair, each said hinge comprising a pair of juxtaposed hinge plates adapted to pivot and slide with respect to each other, one of said plates being secured to said ankle section and the other being secured to the corresponding foot section, each said plate having a pivot face in opposition to a pivot face on the juxtaposed plate, a concave recess in at least one of said faces, a single pivot bearing ball positioned between said opposed faces and retained in said concave recess, means resiliently biasing said hinge plates together against said pivot bearing ball when said ball is positioned in said recess between said opposing faces, means biasing said foot section plate upwardly with respect to said ankle section plate, and means on said ankle section plate for engaging said foot section plate for limiting relative movement therebetween, whereby said pivot bearing ball provides a floating pivot axis for hinge rotation of said hinge plates and thereby said brace arms relative to each other, said concave recess allowing said hinge plates to slide relative to each other and simultaneously pivot relative to each other about said floating pivot axis provided by said ball during limited flexion, extension and twisting of the wearer's foot.

* * * * *

UNITED STATES PATENT AND TRADEMARK OFFICE
CERTIFICATE OF CORRECTION

PATENT NO.   :   5,094,232
DATED        :   March 10, 1992
INVENTOR(S)  :   David P. Harris et al.

It is certified that error appears in the above-identified patent and that said Letters Patent is hereby corrected as shown below:

ON THE TITLE PAGE

Abstract, line 8, insert --a-- after the word includes --.

Column 10, line 19, "as" should read --a--.

Signed and Sealed this

Tenth Day of August, 1993

Attest:

MICHAEL K. KIRK

Attesting Officer       Acting Commissioner of Patents and Trademarks